(12) United States Patent  
Kawada et al.

(10) Patent No.: US 8,993,967 B2
(45) Date of Patent: Mar. 31, 2015

(54) ELECTROMAGNETIC WAVE DETECTION DEVICE

(75) Inventors: Yoichi Kawada, Hamamatsu (JP); Takashi Yasuda, Hamamatsu (JP); Hironori Takahashi, Hamamatsu (JP); Toru Matsumoto, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 381 days.

(21) Appl. No.: 13/583,675

(22) PCT Filed: Feb. 1, 2011

(86) PCT No.: PCT/JP2011/052048
§ 371 (c)(1),
(2), (4) Date: Sep. 10, 2012

(87) PCT Pub. No.: WO2011/122095
PCT Pub. Date: Oct. 6, 2011

(65) Prior Publication Data
US 2012/0326041 A1  Dec. 27, 2012

(30) Foreign Application Priority Data
Mar. 31, 2010  (JP) ................................ 2010-083766

(51) Int. Cl.
*G01N 21/35*  (2014.01)
*G01N 21/3581*  (2014.01)
*G01N 21/21*  (2006.01)

(52) U.S. Cl.
CPC ............ *G01N 21/3581* (2013.01); *G01N 21/21* (2013.01)
USPC ........................................................ 250/353

(58) Field of Classification Search
USPC ........................................................ 250/353
See application file for complete search history.

(56) References Cited

U.S. PATENT DOCUMENTS

| 6,424,665 B1 * | 7/2002 | Kwiat et al. ..................... 372/21 |
| 2004/0246582 A1 * | 12/2004 | Du et al. ......................... 359/497 |
| 2008/0265165 A1 * | 10/2008 | Yeh et al. ................... 250/341.1 |
| 2013/0222801 A1 * | 8/2013 | Harel et al. ..................... 356/328 |
| 2013/0240740 A1 * | 9/2013 | Ouchi ........................... 250/353 |

FOREIGN PATENT DOCUMENTS

| EP | 2072997 A1 * | 6/2009 |
| JP | 2008-96210 | 4/2008 |
| JP | 2009-192524 | 8/2009 |
| JP | 2009-259893 | 11/2009 |
| JP | 2011215382 A * | 10/2011 |
| WO | 2008/044424 | 4/2008 |

* cited by examiner

*Primary Examiner* — Christine Sung
(74) *Attorney, Agent, or Firm* — Drinker Biddle & Reath LLP (57) ABSTRACT

Probe light pulses output from a light source are input to an optical effect unit after the beam diameter is changed by a beam diameter changing optical system, the pulse front is tilted by a pulse front tilting unit, and the beam diameter is adjusted by a beam diameter adjusting optical system. To the optical effect unit, probe light pulses output from the beam diameter adjusting optical system are input, and an electromagnetic wave being an object to be detected is also input. Optical characteristics of the optical effect unit change due to propagation of the electromagnetic wave, and probe light pulses affected by the change in optical characteristics are output from the optical effect unit. The probe light pulses output from the optical effect unit are detected by a photodetector.

10 Claims, 4 Drawing Sheets

ELECTROMAGNETIC WAVE DETECTION DEVICE

TECHNICAL FIELD

The present invention relates to an electromagnetic wave detection device for detecting an electromagnetic wave input to an optical effect unit by probe light pulses.

BACKGROUND ART

As an electromagnetic wave detecting device for detecting an electromagnetic wave input to an optical effect unit by probe light pulses, for example, a device for measuring a terahertz wave temporal waveform by a single probe light pulse has been known (Patent Document 1). Terahertz waves are electromagnetic waves having a frequency of approximately 0.01 THz to 1000 THz corresponding to an intermediate range between light waves and radio waves, and have intermediate characteristics between light waves and radio waves. As application of such a terahertz wave, a technique for obtaining information on an object to be measured by measuring a temporal waveform of an electric field amplitude of a terahertz wave generated in, transmitted through, or reflected on the object to be measured has been studied.

In such an electromagnetic wave detection device, the pulse front of probe light pulses is tilted by a pulse front tilting unit, and then the probe light pulses are input to the optical effect unit in some cases. Also, in some cases, the pulse front of probe light pulses is tilted by a pulse front tilting unit, the beam diameter of the probe light pulses with a tilted pulse front is adjusted by a beam diameter adjusting optical system, and then the probe light pulses are input to the optical effect unit.

The pulse front tilt angle (tilt angle with respect to a plane normal to a principal ray direction) $\gamma$ of light pulses to be output from the pulse front tilting unit is expressed by formula $\tan \gamma = \lambda \cdot d\phi/d\lambda$. $\lambda$ means the wavelength of light pulses, and $d\phi/d\lambda$ means angular dispersion of the pulse front tilting unit at the wavelength $\lambda$.

When the beam diameter of light pulses with a tilted pulse front is enlarged or reduced by the beam diameter adjusting optical system, the pulse front tilt angle of the light pulses changes. At this time, the change in the pulse front tilt angle of the light pulses is according to the ratio of enlargement or reduction in the beam diameter of light pulses by the beam diameter adjusting optical system.

CITATION LIST

Patent Literature

Patent Document 1: Japanese Patent Application Laid-Open No. 2008-096210

SUMMARY OF INVENTION

Technical Problem

Generally, when detecting an electromagnetic wave in an optical effect unit, it is necessary to appropriately set the measurement time range and interaction area by probe light pulses in the optical effect unit, and for that purpose, it is necessary to appropriately set the pulse front tilt angle and beam diameter of probe light pulses to be input to the optical effect unit. The measurement time range T is expressed by formula $T = \sigma \cdot \tan \gamma / c$. $\sigma$ means the beam diameter of probe light pulses, and c means light speed. The interaction area depends on the beam diameter of the probe light pulses.

However, as described above, when the beam diameter adjusting optical system is provided at a stage subsequent to the pulse front tilting unit in the electromagnetic wave detection device, the pulse front tilt angle and beam diameter of probe light pulses to be input to the optical effect unit cannot be set respectively and independently, and if one changes, the other also changes, so that it is difficult to set these to appropriate values, respectively.

The present invention has been made to solve the problems described above, and an object thereof is to provide an electromagnetic wave detection device which allows easily setting each of the pulse front tilt angle and beam diameter of probe light pulses to be input to its optical effect unit to appropriate values.

Solution to Problem

An electromagnetic wave detection device of the present invention includes (1) a light source which outputs probe light pulses, (2) a beam diameter changing optical system which changes a beam diameter of the probe light pulses output from the light source, (3) a pulse front tilting unit which tilts a pulse front of the probe light pulses output from the beam diameter changing optical system, (4) a beam diameter adjusting optical system which adjusts a beam diameter of the probe light pulses output from the pulse front tilting unit, (5) an optical effect unit which is input with the probe light pulses output from the beam diameter adjusting optical system and is input with an electromagnetic wave being an object to be detected, optical characteristics of which change due to propagation of the electromagnetic wave, and which outputs the probe light pulses affected by the change in optical characteristics, and (6) a photodetector which detects the probe light pulses output from the optical effect unit.

In the electromagnetic wave detection device of the present invention, probe light pulses output from the light source are input to the optical effect unit after the beam diameter thereof is changed by the beam diameter changing optical system, the pulse front thereof is tilted by the pulse front tilting unit, and the beam diameter thereof is adjusted by the beam diameter adjusting optical system. To the optical effect unit, probe light pulses output from the beam diameter adjusting optical system are input, and an electromagnetic wave being an object to be detected is also input. Optical characteristics of the optical effect unit change due to propagation of the electromagnetic wave, and probe light pulses affected by the change in optical characteristics are output from the optical effect unit. The probe light pulses output from the optical effect unit are detected by the photodetector. Based on the probe light pulse detection result by the photodetector, the electromagnetic wave input to the optical effect unit is detected.

In the electromagnetic wave detection device of the present invention, an image by the beam diameter changing optical system may be located on the pulse front tilting unit. Moreover, the beam diameter adjusting optical system may have an imaging relationship between the pulse front tilting unit and the optical effect unit.

In the electromagnetic wave detection device of the present invention, each of the measurement time range and interaction area by the probe light pulses in the optical effect unit may be adjusted through an enlargement or reduction in the beam diameter of the probe light pulses by each of the beam diameter changing optical system and the beam diameter adjusting optical system and a tilt of the pulse front of the probe light pulses by the pulse front tilting unit.

The electromagnetic wave detection device of the present invention may further include a probe light pulse beam diameter changing optical system which is provided on an optical path of the probe light pulses between the optical effect unit and the photodetector, and changes a beam diameter of the probe light pulses. At this time, the probe light pulse beam diameter changing optical system may have an imaging relationship between the optical effect unit and the photodetector.

The electromagnetic wave detection device of the present invention may further include an electromagnetic wave beam diameter changing optical system which changes a beam diameter of the electromagnetic wave to be input to the optical effect unit. At this time, an image plane by the electromagnetic wave beam diameter changing optical system may be located on the optical effect unit.

The electromagnetic wave detection device of the present invention may further include a timing adjuster unit which adjusts relative input timing between the probe light pulses and the electromagnetic wave when each of the probe light pulses and the electromagnetic wave is input to the optical effect unit.

The electromagnetic wave detection device of the present invention may further include (a) a pump light pulse irradiating unit which converges and irradiates pump light pulses onto an object to be measured and scans said converging and irradiating position in the object to be measured, (b) generate a terahertz wave in the object to be measured by converging and irradiating pump light pulses onto the object to be measured by the pump light pulse irradiating unit, and (c) input the terahertz wave and the probe light pulses to the optical effect unit, and (d) the photodetector may detect the probe light pulses output from the optical effect unit in terms of each converging and irradiating position onto the object to be measured by the pump light pulse irradiating unit.

Advantageous Effects of Invention

According to the present invention, each of the pulse front tilt angle and beam diameter of probe light pulses to be input to the optical effect unit can be easily set to appropriate values.

DESCRIPTION OF EMBODIMENTS

Hereinafter, modes for carrying out the present invention will be described in detail with reference to the accompanying drawings. Also, the same elements will be denoted with the same reference signs in the description of drawings, and overlapping description will be omitted.

First Embodiment

Figure 1:
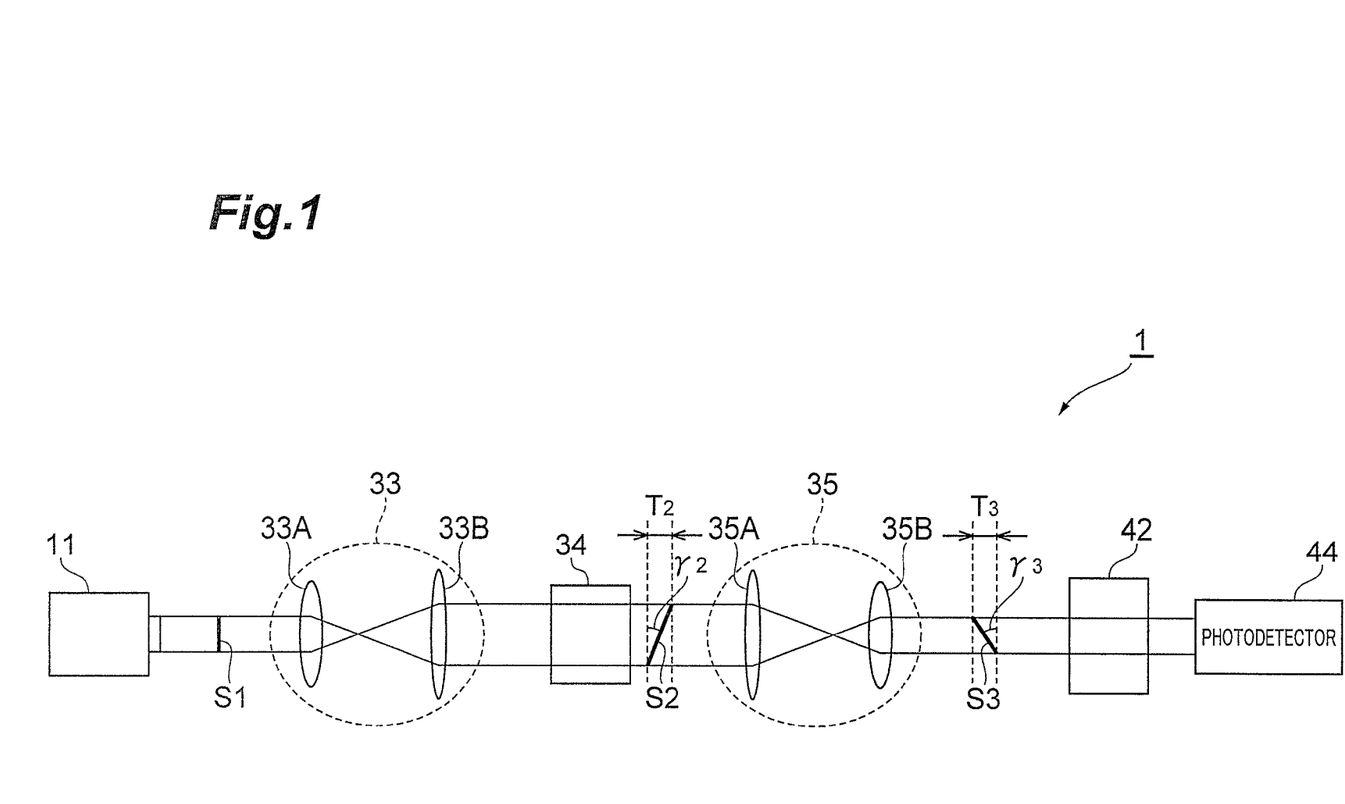
FIG. 1 is a configuration diagram of an electromagnetic wave detection device 1 of a first embodiment.

FIG. 1 is a configuration diagram of an electromagnetic wave detection device 1 of a first embodiment. The electromagnetic wave detection device 1 of the first embodiment includes a light source 11, a beam diameter changing optical system 33, a pulse front tilting unit 34, a beam diameter adjusting optical system 35, an optical effect unit 42, and a photodetector 44.

The light source 11 outputs probe light pulses, and is preferably a femtosecond pulsed laser light source which outputs a pulsed laser light whose pulse width is on the order of femtoseconds. The beam diameter changing optical system 33 changes the beam diameter of probe light pulses output from the light source 11. The beam diameter changing optical system 33 includes a lens 33A and a lens 33B. The rear focal position of the front-stage lens 33A and the front focal position of the rear-stage lens 33B are coincident with each other. The beam diameter changing optical system 33 can change the beam diameter of probe light pulses according to the ratio of a focal length of the front-stage lens 33A and a focal length of the rear-stage lens 33B.

The pulse front tilting unit 34 tilts the pulse front of probe light pulses output from the beam diameter changing optical system 33. The pulse front tilting unit 34 can tilt the pulse front of probe light pulses by use of, for example, a prism, a grism, a reflective diffraction grating, a transmissive diffraction grating, or a spatial light modulator. The pulse front means a plane connecting positions indicating the maximum powers on a beam line of light pulses at a certain moment. On the other hand, the wave front means an equiphase plane of light.

The beam diameter adjusting optical system 35 adjusts the beam diameter of probe light pulses output from the pulse front tilting unit 34. The beam diameter adjusting optical system 35 includes a lens 35A and a lens 35B. The rear focal position of the front-stage lens 35A and the front focal position of the rear-stage lens 35B are coincident with each other. The beam diameter adjusting optical system 35 can adjust the beam diameter of probe light pulses according to the ratio of a focal length of the front-stage lens 35A and a focal length of the rear-stage lens 35B.

The optical effect unit 42 is input with probe light pulses output from the beam diameter adjusting optical system 35 and is also input with an electromagnetic wave being an object to be detected, changes in optical characteristics due to propagation of the electromagnetic wave, and outputs probe light pulses affected by the change in optical characteristics. For example, the electromagnetic wave as an object to be detected is a terahertz wave and the optical effect unit 42 is made of nonlinear optical crystal such as ZnTe crystal or organic crystal.

The photodetector 44 detects probe light pulses output from the optical effect unit 42. Based on the probe light pulse detection result by the photodetector 44, the electromagnetic wave input to the optical effect unit 42 is detected.

Each of the beam diameter changing optical system 33 and the beam diameter adjusting optical system 35 may be composed of a lens pair or may be composed of a curved mirror pair. Each of the beam diameter changing optical system 33 and the beam diameter adjusting optical system 35 may be an enlarging optical system or may be a reducing optical system. Moreover, the whole of the beam diameter changing optical system 33 and the beam diameter adjusting optical system 35 may be an enlarging optical system or may be a reducing optical system.

In this electromagnetic wave detection device 1, probe light pulses output from the light source 11 are input to the optical effect unit 42 after the beam diameter thereof is changed by the beam diameter changing optical system 33, the pulse front thereof is tilted by the pulse front tilting unit 34, and the beam diameter thereof is adjusted by the beam diameter adjusting optical system 35. To the optical effect unit 42, probe light pulses output from the beam diameter adjusting optical system 35 are input, and an electromagnetic wave being an object to be detected is also input. Optical characteristics of the optical effect unit 42 change due to propagation of the electromagnetic wave, and probe light pulses affected by the change in optical characteristics are output from the optical effect unit 42. The probe light pulses output from the optical effect unit 42 are detected by the photodetector 44. Based on the probe light pulse detection result by the photodetector 44, the electromagnetic wave input to the optical effect unit 42 is detected.

A pulse front S1 of probe light pulses output from the light source 11 until being input to the pulse front tilting unit 34 is parallel to a plane normal to the principal ray direction, and has a tilt angle of 0 degrees. A pulse front S2 of probe light pulses output from the pulse front tilting unit 34 until being input to the beam diameter adjusting optical system 35 tilts by a tilt angle $\gamma 2$ with respect to a plane normal to the principal ray direction. A pulse front S3 of probe light pulses output from the beam diameter adjusting optical system 35 to be input to the optical effect unit 42 tilts by a tilt angle $\gamma 3$ with respect to a plane normal to the principal ray direction. Here, the time range T2 of the pulse front S2 and the time range T3 of the pulse front S3 are equal to each other.

The tilt angle $\gamma 2$ of the pulse front S2 is determined depending on the wavelength of probe light pulses and angular dispersion of the pulse front tilting unit 34 without depending on whether the beam diameter changing optical system 33 exists. The change from the tilt angle $\gamma 2$ of the pulse front S2 to the tilt angle $\gamma 3$ of the pulse front S3 is according to the ratio of enlargement or reduction in the beam diameter of probe light pulses by the beam diameter adjusting optical system 35. That is, the tilt angle $\gamma 3$ of the pulse front S3 of probe light pulses to be input to the optical effect unit 42 is determined based on the wavelength of probe light pulses, the angular dispersion of the pulse front tilting unit 34, and the enlargement or reduction ratio of the beam diameter adjusting optical system 35. On the other hand, the beam diameter of probe light pulses to be input to the optical effect unit 42 is determined based on the enlargement or reduction ratio of the whole of the beam diameter changing optical system 33 and the beam diameter adjusting optical system 35.

Therefore, the electromagnetic wave detection device 1 can set each of the pulse front tilt angle and beam diameter of probe light pulses to be input to the optical effect unit 42 to appropriate values independently of each other through an enlargement or reduction in the beam diameter of probe light pulses by each of the beam diameter changing optical system 33 and the beam diameter adjusting optical system 35 and a tilt of the pulse front of probe light pulses by the pulse front tilting unit 34, and can appropriately set the measurement time range T and interaction area by probe light pulses in the optical effect unit 42.

Suppose, for example, a case where the center wavelength of probe light pulses is 800 nm, the beam diameter of probe light pulses to be input to the beam diameter changing optical system 33 is 1 mm, and a 1250 grooves/mm-diffraction grating is used as the pulse front tilting unit 34. If the enlargement ratio in the beam diameter of the beam diameter changing optical system 33 is provided as 1.5 times and the reduction ratio in the beam diameter of the beam diameter adjusting optical system 35 is provided as 0.67 times, the measurement time range T by probe light pulses output from the beam diameter adjusting optical system 35 can be provided as 5 ps, and the beam diameter can be provided as 1 mm. Moreover, if the enlargement ratio in the beam diameter of the beam diameter changing optical system 33 is provided as 5.22 times and the reduction ratio in the beam diameter of the beam diameter adjusting optical system 35 is provided as 0.2 times, the measurement time range T by probe light pulses output from the beam diameter adjusting optical system 35 can be provided as 30 ps, and the beam diameter can be provided as 1 mm.

In the present embodiment, the pulse front tilt angle can be adjusted without changing the type (for example, when a diffraction grating is used as the pulse front tilting unit 34, the number of rulings per unit length and the like of the diffraction grating) of the pulse front tilting unit 34. Among diffractive optical elements used as the pulse front tilting unit 34, one having a large angular dispersion (that is, one that can tilt the pulse front at a large tilt angle) is generally expensive and low in light use efficiency, but in the present embodiment, the tilt angle of the pulse front can be adjusted while using a diffractive optical element that is high in light use efficiency despite a small angular dispersion.

It is preferable that an image by the beam diameter changing optical system 33 is located on the pulse front tilting unit 34. Moreover, it is preferable that the beam diameter adjusting optical system 35 has an imaging relationship between the pulse front tilting unit 34 and the optical effect unit 42. In doing this, the beam quality of probe light pulses is improved, and an electromagnetic wave (terahertz wave) having high time base accuracy can be detected in the optical effect unit 42.

It is further preferable that each of the beam diameter changing optical system 33 and the beam diameter adjusting optical system 35 is an optical system that eliminates image distortion caused by aberrations such as field curvature, and it is therefore preferable that each of the optical systems is, for example, a 4f optical system.

Moreover, it is preferable that each of the beam diameter changing optical system 33 and the beam diameter adjusting optical system 35 is a zoom lens optical system that can arbitrarily change its enlargement ratio or reduction ratio with the positional relationship between an object plane and an image plane in the above-described imaging relationship kept. In doing this, the arbitrary pulse front tilt angle and beam diameter can be easily changed.

Second Embodiment

Figure 2:
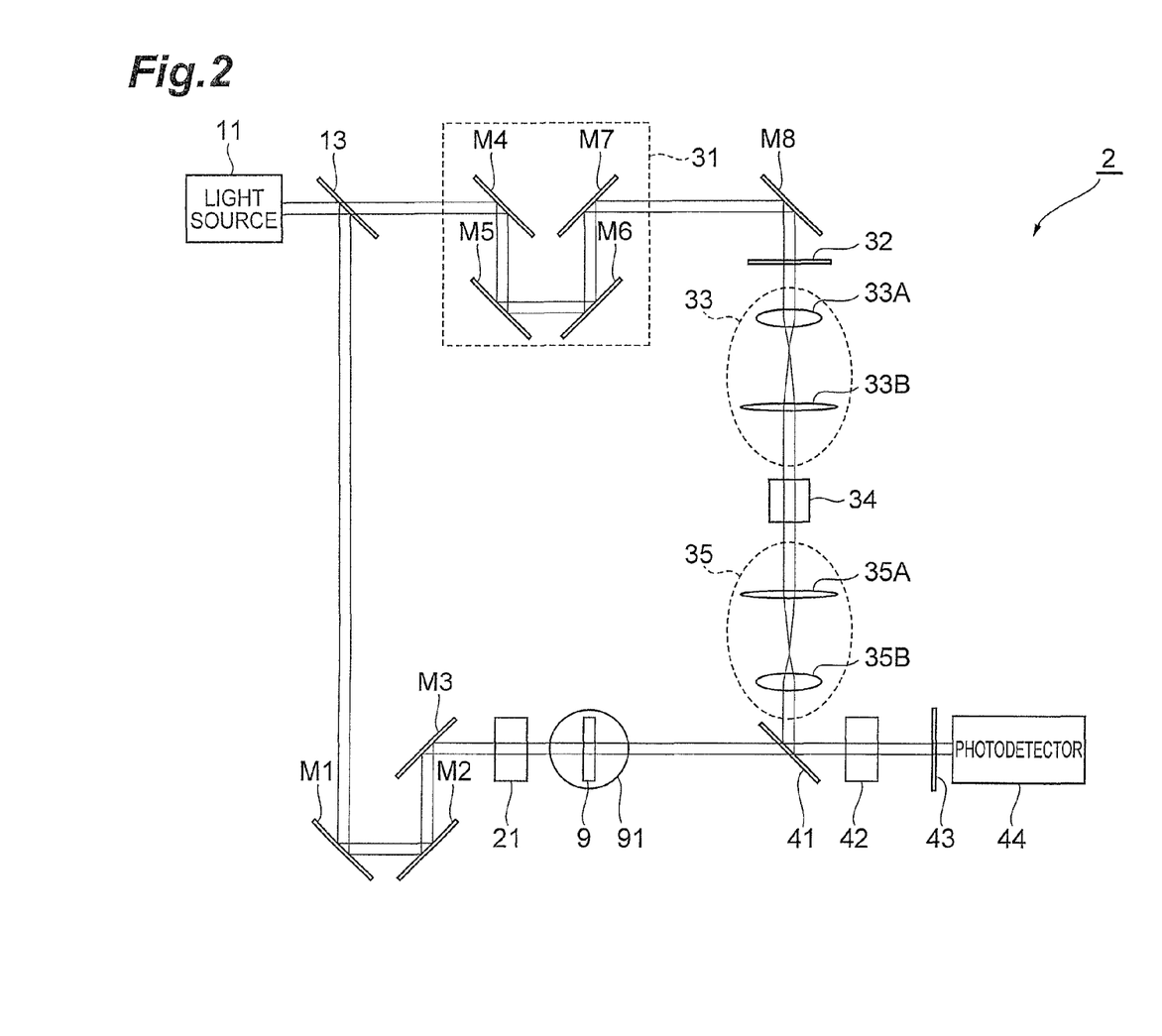
FIG. 2 is a configuration diagram of an electromagnetic wave detection device 2 of a second embodiment.

FIG. 2 is a configuration diagram of an electromagnetic wave detection device 2 of a second embodiment. The electromagnetic wave detection device 2 of the second embodiment detects a terahertz wave in an optical effect unit 42 as an electromagnetic wave of an object to be detected, and includes a light source 11, a separator unit 13, a terahertz wave generator unit 21, a timing adjuster unit 31, a polarizer 32, a beam diameter changing optical system 33, a pulse front tilting unit 34, a beam diameter adjusting optical system 35, a wave synthesizer unit 41, an optical effect unit 42, an analyzer 43, a photodetector 44, and mirrors M1 to M8.

The separator unit 13 is, for example, a beam splitter, and separates light pulses output from the light source 11 into two parts, outputs either one of the two separated parts of light pulses as pump light pulses to the mirror M1, and outputs the other as probe light pulses to the mirror M4.

The pump light pulses output from the separator unit 13 are sequentially reflected by the mirrors M1 to M3, and input to the terahertz wave generator unit 21. In addition, the optical system for the pump light pulses from the separator unit 13 to the terahertz wave generator unit 21 will be referred to as a "pump light pulse optical system" in the following.

The terahertz wave generator unit 21 generates and outputs a pulsed terahertz wave in response to an input of the pump light pulses, and includes, for example, any of the nonlinear optical crystal, optical antenna element, semiconductor, and superconductor. When the terahertz wave generator unit 21 includes nonlinear optical crystal, the terahertz wave generator unit 21 can generate a terahertz wave by a nonlinear optical phenomenon that develops with incidence of the pump light pulses.

Terahertz waves are electromagnetic waves having a frequency of approximately 0.01 THz to 1000 THz corresponding to an intermediate range between light waves and radio waves, and have intermediate characteristics between light waves and radio waves. Moreover, the pulse width of a pulsed terahertz wave is on the order of a few picoseconds. The terahertz wave output from the terahertz wave generator unit 21 obtains information (for example, an adsorption coefficient, a refractive index) on an object to be measured 9 placed on a sample base 91 by being transmitted through the object to be measured 9, and are thereafter input to the wave synthesizer unit 41. The object to be measured 9 is placed on the sample base 91, and can be adjusted in pulsed terahertz wave incident position by a movement of the sample base 91. In addition, the optical system for the terahertz wave from the terahertz wave generator unit 21 to the wave synthesizer unit 41 will be referred to as a "terahertz wave optical system" in the following.

On the other hand, the probe light pulses output from the separator unit 13 are sequentially reflected by the mirrors M4 to M8, pass through the polarizer 32, the beam diameter changing optical system 33, the pulse front tilting unit 34, and the beam diameter adjusting optical system 35 in order, and are input to the wave synthesizer unit 41. The pulse front tilting unit 34 tilts the pulse front of probe light pulses to make the pulse fronts of a terahertz wave and probe light pulses when being input to the optical effect unit 42 unparallel to each other. In addition, the optical system for the probe light pulses from the separator unit 13 to the wave synthesizer unit 41 will be referred to as a "probe light pulse optical system" in the following. The polarizer 32 can be disposed at an arbitrary position on the probe light pulse optical system.

The four mirrors M4 to M7 compose the timing adjuster unit 31. In other words, by movement of the mirrors M5 and M6, the optical path length between the mirrors M4 and M7 and the mirrors M5 and M6 is adjusted, whereby the optical path length of the probe light pulse optical system is adjusted. Accordingly, the timing adjuster unit 31 can adjust the relative input timing between probe light pulses and a terahertz wave when each of these is input to the optical effect unit 42 by adjusting the difference between the optical path length of the pump light pulse optical system and terahertz wave optical system from the separator unit 13 to the wave synthesizer unit 41 and the optical path length of the probe light pulse optical system from the separator unit 13 to the wave synthesizer unit 41.

The wave synthesizer unit 41 is input with a terahertz wave output from the terahertz wave generator unit 21 and transmitted through the object to be measured 9 and probe light pulses output from the beam diameter adjusting optical system 35, and outputs the terahertz wave and probe light pulses to the optical effect unit 42 after synthesizing these so as to be coaxial with each other. The wave synthesizer unit 41 is preferably a pellicle.

The optical effect unit 42 is input with the terahertz wave and probe light pulses output from the wave synthesizer unit 41, has birefringence induced by propagation of the terahertz wave, changes the polarization state of probe light pulses by the birefringence, and outputs the probe light pulses to the analyzer 43. The photodetector 44 receives the probe light pulses output from the optical effect unit 42 and passed through the analyzer 43, and detects an intensity distribution of the received probe light pulses. The polarizer 32, the analyzer 43, and the photodetector 44 detect a one-dimensional distribution or two-dimensional distribution of polarization state changes in a beam cross-section of the probe light pulses output from the optical effect unit 42.

Also in the electromagnetic wave detection device 2 of the second embodiment, each of the pulse front tilt angle and beam diameter of probe light pulses to be input to the optical effect unit 42 can be set to appropriate values independently of each other through an enlargement or reduction in the beam diameter of probe light pulses by each of the beam diameter changing optical system 33 and the beam diameter adjusting optical system 35 and a tilt of the pulse front of probe light pulses by the pulse front tilting unit 34, and a measurement time range T and interaction area by probe light pulses in the optical effect unit 42 can be appropriately set.

Also in the second embodiment, it is preferable that an image by the beam diameter changing optical system 33 is located on the pulse front tilting unit 34. Moreover, it is preferable that the beam diameter adjusting optical system 35 has an imaging relationship between the pulse front tilting unit 34 and the optical effect unit 42. In doing this, the beam quality of probe light pulses is improved, and an electromagnetic wave (terahertz wave) having high time base accuracy can be detected in the optical effect unit 42.

It is further preferable that each of the beam diameter changing optical system 33 and the beam diameter adjusting optical system 35 is an optical system that eliminates image distortion caused by aberrations such as field curvature, and it is therefore preferable that each of the optical systems is, for example, a 4f optical system.

Moreover, it is preferable that each of the beam diameter changing optical system 33 and the beam diameter adjusting optical system 35 is a zoom lens optical system that can arbitrarily change its enlargement ratio or reduction ratio with the positional relationship between an object plane and an image plane in the above-described imaging relationship kept. In doing this, the arbitrary pulse front tilt angle and beam diameter can be easily changed.

Third Embodiment

Figure 3:
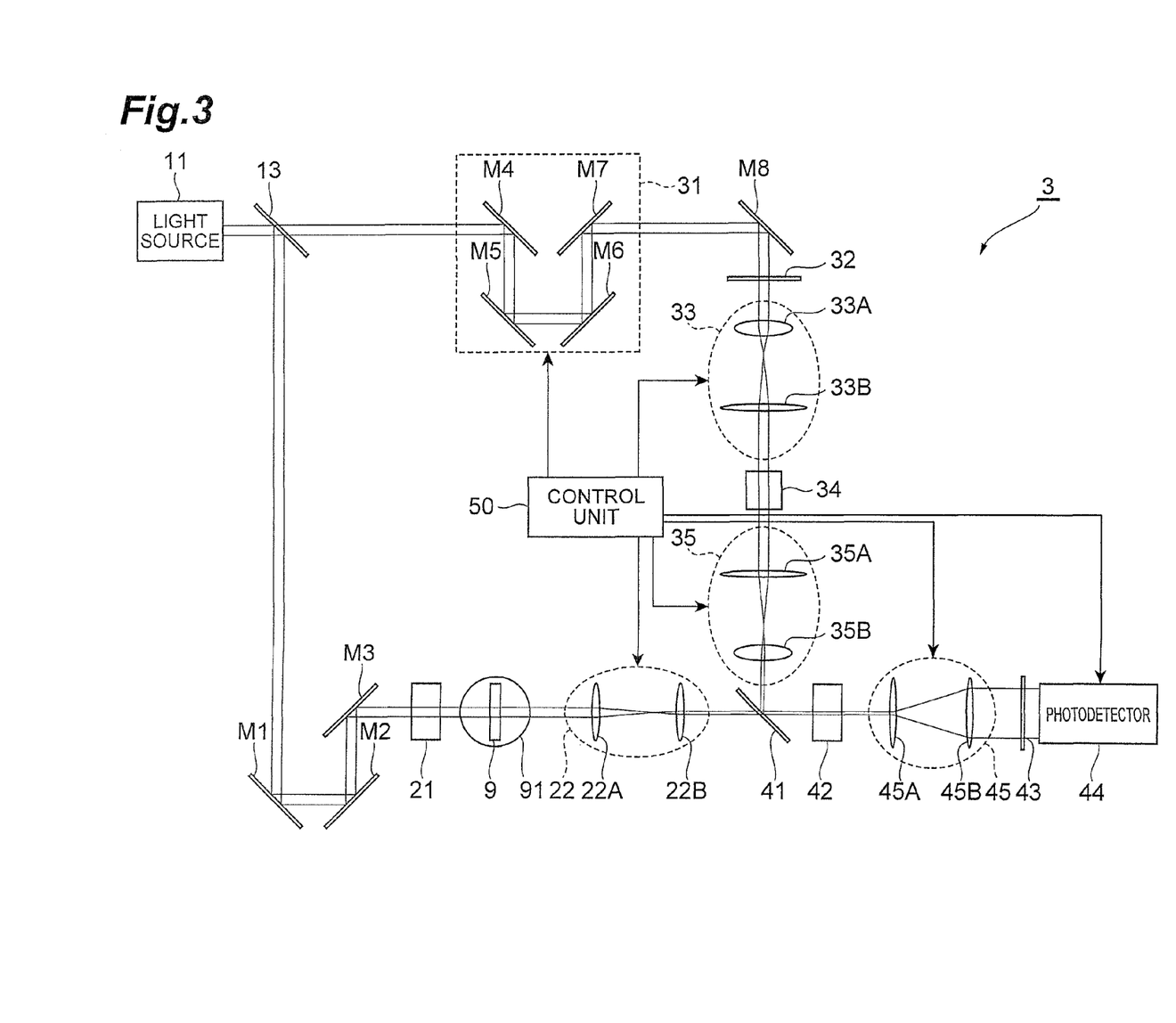
FIG. 3 is a configuration diagram of an electromagnetic wave detection device 3 of a third embodiment.

FIG. 3 is a configuration diagram of an electromagnetic wave detection device 3 of a third embodiment. The electromagnetic wave detection device 3 of the third embodiment further includes a terahertz wave beam diameter changing optical system (electromagnetic wave beam diameter changing optical system) 22, a probe light pulse beam diameter changing optical system 45, and a control unit 50 in addition to the configuration of the electromagnetic wave detection device 2 of the second embodiment shown in FIG. 2.

The terahertz wave beam diameter changing optical system 22 is provided on an optical path of a terahertz wave between the object to be measured 9 and the wave synthesizer unit 41, and changes the beam diameter of the terahertz wave to be input to the optical effect unit 42. The terahertz wave beam diameter changing optical system 22 includes a lens 22A and a lens 22B. The rear focal position of the front-stage lens 22A and the front focal position of the rear-stage lens 22B are coincident with each other. The terahertz wave beam diameter changing optical system 22 can change the beam diameter of a terahertz wave according to the ratio of a focal length of the front-stage lens 22A and a focal length of the rear-stage lens 22B.

It is preferable that the terahertz wave beam diameter changing optical system 22 has an imaging relationship between the object to be measured 9 and the optical effect unit 42. It is further preferable that the terahertz wave beam diameter changing optical system 22 is an optical system that eliminates image distortion caused by aberrations such as field curvature, and it is therefore preferable that the terahertz wave beam diameter changing optical system 22 is, for example, a 4f optical system.

Moreover, it is preferable that the terahertz wave beam diameter changing optical system 22 is a zoom lens optical system that can arbitrarily change its enlargement ratio or reduction ratio with the positional relationship between an object plane and an image plane in the above-described imaging relationship kept. In doing this, an optimal beam diameter of a terahertz wave can be set in accordance with the beam diameter of probe light pulses.

As a result of the terahertz wave beam diameter changing optical system 22 being provided, the relationship of beam diameters of each of the terahertz wave and probe light to be input to the optical effect unit 42 can be adjusted. That is, the beam diameter of probe light pulses on the optical effect unit 42 has been changed by the beam diameter changing optical system 33 and the beam diameter adjusting optical system 35. Therefore, as a result of the beam diameter of a terahertz wave being changed by the terahertz wave beam diameter changing optical system 22 in accordance with the change in the beam diameter of probe light pulses, the terahertz wave can be efficiently detected in the optical effect unit 42.

It is not always necessary that the beam diameter of a terahertz wave and the beam diameter of probe light pulses are coincident in the optical effect unit 42. For example, when a terahertz wave has a Gaussian intensity distribution in a beam plane, by making the beam diameter of the terahertz wave in the optical effect unit 42 larger than the beam diameter of the probe light pulses in the optical effect unit 42, the probe light pulses probe only a center part in the Gaussian distribution of the terahertz wave. Measurement error in single terahertz wave temporal waveform measurement caused by the terahertz wave having a Gaussian intensity distribution in a beam plane can be reduced.

The probe light pulse beam diameter changing optical system 45 is provided on an optical path of probe light pulses between the optical effect unit 42 and the photodetector 44, and changes (enlarges or reduces) the beam diameter of the probe light pulses. The probe light pulse beam diameter changing optical system 45 includes a lens 45A and a lens 45B. The rear focal position of the front-stage lens 45A and the front focal position of the rear-stage lens 45B are coincident with each other. The probe light pulse beam diameter changing optical system 45 can change the beam diameter of probe light pulses according to the ratio of a focal length of the front-stage lens 45A and a focal length of the rear-stage lens 45B.

The number of pixels of the photodetector 44 corresponds to the time resolution of a terahertz wave temporal waveform to be measured. Because the number of pixels and pixel pitch vary depending on the photodetector, the temporal waveform can be measured with a desirable time resolution by providing the probe light pulse beam diameter changing optical system 45. The probe light pulse beam diameter changing optical system 45 may be for independent beam diameter changes in the vertical direction and horizontal direction of a beam cross-section of probe light pulses. The analyzer 43 may be provided at a stage previous to the probe light pulse beam diameter changing optical system 45 or may be provided at a stage subsequent to the probe light pulse beam diameter changing optical system 45.

It is preferable that the probe light pulse beam diameter changing optical system 45 has an imaging relationship between the optical effect unit 42 and the photodetector 44. It is further preferable that the probe light pulse beam diameter changing optical system 45 is an optical system that eliminates image distortion caused by aberrations such as field curvature, and it is therefore preferable that the probe light pulse beam diameter changing optical system 45 is, for example, a 4f optical system.

Moreover, it is preferable that the probe light pulse beam diameter changing optical system 45 is a zoom lens optical system that can arbitrarily change its enlargement ratio or reduction ratio with the positional relationship between an object plane and an image plane in the above-described imaging relationship kept. In doing this, an optimal beam diameter of probe light pulses can be set in accordance with the size of a light receiving surface of the photodetector 44.

It is preferable that each of the beam diameter changing optical system 33, the beam diameter adjusting optical system 35, the terahertz wave beam diameter changing optical system 22, and the probe light pulse beam diameter changing optical system 45 is controlled in zooming function by receiving a control signal to be adjusted in the enlargement ratio or reduction ratio. The control unit 50 gives a control signal to each of the beam diameter changing optical system 33, the beam diameter adjusting optical system 35, the terahertz wave beam diameter changing optical system 22, and the probe light pulse beam diameter changing optical system 45 to thereby control the zooming function of these optical systems and set the enlargement ratio or reduction ratio. Moreover, the control unit 50 controls the position of the mirrors M5 and M6 in the timing adjuster unit 31 to adjust the relative input timing between the probe light pulses and terahertz wave when each of these is input to the optical effect unit 42. Moreover, the control unit 50 controls the timing of a light pulse output from the light source 11, and controls the timing of probe light pulse detection by the photodetector 44.

As a result of including such a control unit 50, the electromagnetic wave detection device 3 can perform the following operation. First, the enlargement ratio of the beam diameter changing optical system 33 is increased to enlarge the time range (that is, the measurement time range T in single terahertz wave temporal waveform measurement) where probe light pulses exist. At this time, the beam diameter adjusting optical system 35, the probe light pulse beam diameter changing optical system 45, and the terahertz wave beam diameter changing optical system 22 adjust or change the beam diameter of each of the probe light pulses and terahertz wave so that the terahertz wave can be measured most efficiently and at the highest time resolution.

Thereafter, by controlling the timing adjuster unit 31, the relative input timing between the probe light pulses and terahertz wave when each of these is input to the optical effect unit 42 is adjusted to move the measurement time position for a terahertz wave desired to be measured to a predetermined position in the terahertz wave measurement time range.

Finally, the enlargement ratio of the beam diameter changing optical system 33 is changed so as to reach a measurement time range T for the terahertz wave desired to be measured. At this time, the beam diameter adjusting optical system 35, the probe light pulse beam diameter changing optical system 45, and the terahertz wave beam diameter changing optical system 22 adjust or change the beam diameter of each of the probe light pulses and terahertz wave so that the terahertz wave can be measured most efficiently and at the highest time resolution.

In doing this, for example, even when the refractive index or thickness of the object to be measured 9 is unknown and it is difficult to determine the terahertz wave measurement time range, time delay of a terahertz wave can be easily monitored, and the terahertz wave measurement time range can be determined.

It is preferable that the operation of each of the beam diameter changing optical system 33, the beam diameter adjusting optical system 35, the probe light pulse beam diameter changing optical system 45, the terahertz wave beam diameter changing optical system 22, and the timing adjuster unit 31 as described above is automatically optimized based on a signal of a detected terahertz wave temporal waveform and the like.

Fourth Embodiment

Figure 4:
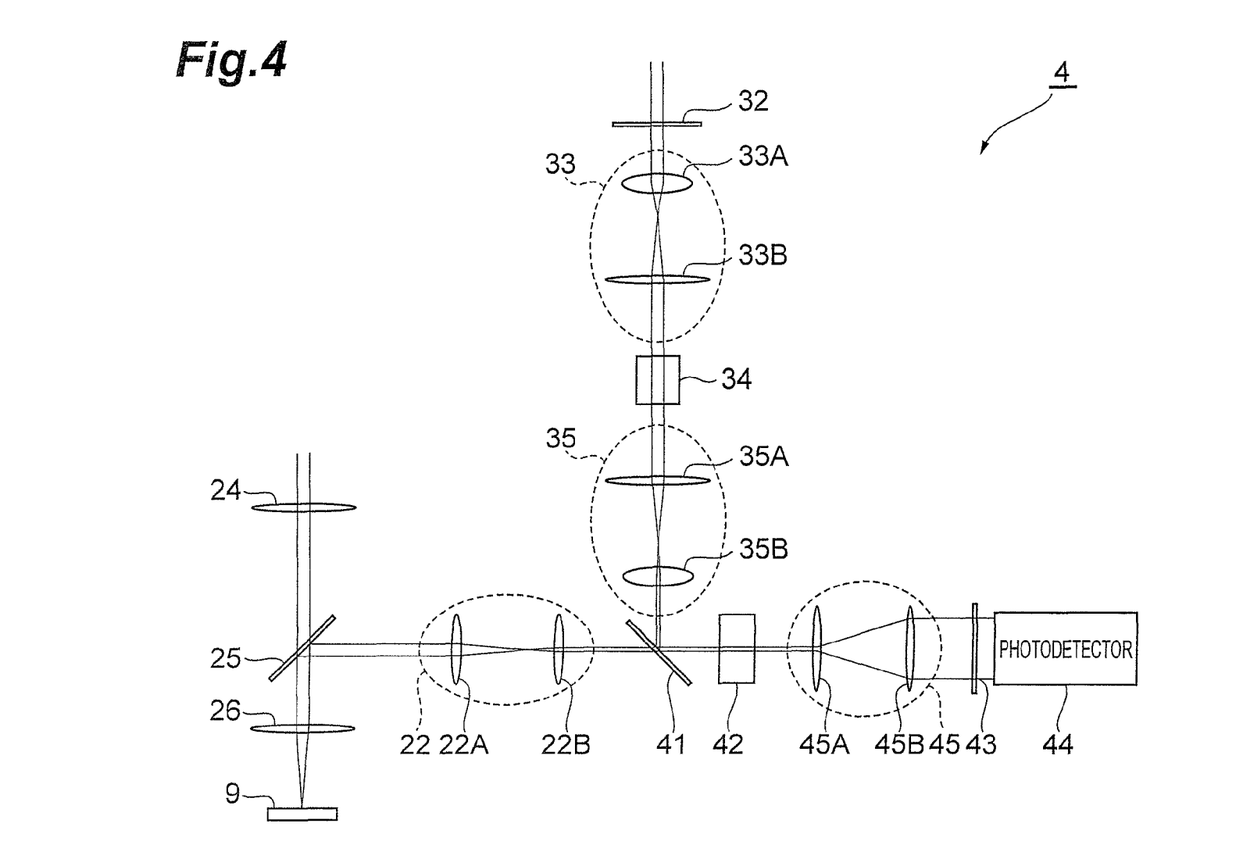
FIG. 4 is a configuration diagram of an electromagnetic wave detection device 4 of a fourth embodiment.

FIG. 4 is a configuration diagram of an electromagnetic wave detection device 4 of a fourth embodiment. The electromagnetic wave detection device 4 of the fourth embodiment shown in this figure has the configuration of the electromagnetic wave detection device 3 of the third embodiment shown in FIG. 3, in which the object to be measured 9 serves as a terahertz wave generator unit 21, and includes a lens 24, an ITO coated optical plate 25, and an objective lens 26.

The lens 24, the ITO coated optical plate 25, and the objective lens 26 provided in the pump light pulse optical system compose a pump light pulse irradiating unit that converges and irradiates pump light pulses onto the object to be measured 9. Said converging and irradiating position in the object to be measured 9 is two-dimensionally scanned. Scanning of the converging and irradiating position may be carried out by scanning the object to be measured 9 or may be carried out by scanning a principal ray of pump light pulses made incident onto the lens 24.

The object to be measured 9 is, for example, a semiconductor device, and generates a terahertz wave as a result of being irradiated with pump light pulses. The terahertz wave is input to the wave synthesizer unit 41 through the objective lens 26, the ITO coated optical plate 25, and the terahertz wave beam diameter changing optical system 22.

The wave synthesizer unit 41 is input with a terahertz wave generated in the object to be measured 9 as a result of pump light pulses being converged and irradiated onto the object to be measured 9 and probe light pulses output from the beam diameter adjusting optical system 35, and outputs the terahertz wave and probe light pulses to the optical effect unit 42 after synthesizing these so as to be coaxial with each other.

The optical effect unit 42 is input with the terahertz wave and probe light pulses output from the wave synthesizer unit 41, has birefringence induced by propagation of the terahertz wave, changes the polarization state of probe light pulses by the birefringence, and outputs the probe light pulses to the analyzer 43.

The photodetector 44 receives the probe light pulses output from the optical effect unit 42 and passed through the analyzer 43 and the probe light pulse beam diameter changing optical system 45, and detects an intensity distribution of the received probe light pulses. The polarizer 32, the analyzer 43, and the photodetector 44 detect a one-dimensional distribution or two-dimensional distribution of polarization state changes in a beam cross-section of the probe light pulses output from the optical effect unit 42 in terms of each converging and irradiating position of pump light pulses onto the object to be measured 9.

The electromagnetic wave detection device 4 of the fourth embodiment 4 constructs a so-called laser terahertz emission microscope (LTEM). The LTEM is capable of non-contact measurement of an electric field distribution of an object to be measured which is, for example, a semiconductor device.

The present invention can be applied to an LTEM. Accordingly, an LTEM system which allows arbitrarily adjusting the measurement time range for a terahertz wave temporal waveform in single terahertz wave temporal waveform measurement can be constructed.

REFERENCE SIGNS LIST

1~4: electromagnetic wave detection device, 9: object to be measured, 11: light source, 13: separator unit, 21: terahertz wave generator unit, 22: terahertz wave beam diameter changing optical system (electromagnetic wave beam diameter changing optical system), 24: lens, 25: ITO coated optical plate, 26: objective lens, 31: timing adjuster unit, 32: polarizer, 33: beam diameter changing optical system, 34: pulse front tilting unit, 35: beam diameter adjusting optical system, 41: wave synthesizer unit, 42: optical effect unit, 43: analyzer, 44: photodetector, 45: probe light pulse beam diameter changing optical system, 50: control unit, M1~M8: mirror.

The invention claimed is:

1. An electromagnetic wave detection device comprising:
a light source which outputs probe light pulses;
a beam diameter changing optical system which changes a beam diameter of the probe light pulses output from the light source;
a pulse front tilting unit which tilts a pulse front of the probe light pulses output from the beam diameter changing optical system;
a beam diameter adjusting optical system which adjusts a beam diameter of the probe light pulses output from the pulse front tilting unit;
an optical effect unit which is input with the probe light pulses output from the beam diameter adjusting optical system and is input with an electromagnetic wave being an object to be detected, optical characteristics of which change due to propagation of the electromagnetic wave, and which outputs the probe light pulses affected by the change in optical characteristics; and
a photodetector which detects the probe light pulses output from the optical effect unit.

2. The electromagnetic wave detection device according to claim 1, wherein an image by the beam diameter changing optical system is located on the pulse front tilting unit.

3. The electromagnetic wave detection device according to claim 1, wherein the beam diameter adjusting optical system has an imaging relationship between the pulse front tilting unit and the optical effect unit.

4. The electromagnetic wave detection device according to claim 1, wherein each of the measurement time range and interaction area by the probe light pulses in the optical effect unit is adjusted through an enlargement or reduction in the beam diameter of the probe light pulses by each of the beam diameter changing optical system and the beam diameter adjusting optical system and a tilt of the pulse front of the probe light pulses by the pulse front tilting unit.

5. The electromagnetic wave detection device according to claim 1, further comprising a probe light pulse beam diameter changing optical system which is provided on an optical path of the probe light pulses between the optical effect unit and the photodetector, and changes a beam diameter of the probe light pulses.

6. The electromagnetic wave detection device according to claim 5, wherein the probe light pulse beam diameter changing optical system has an imaging relationship between the optical effect unit and the photodetector.

7. The electromagnetic wave detection device according to claim 1, further comprising an electromagnetic wave beam diameter changing optical system which changes a beam diameter of the electromagnetic wave to be input to the optical effect unit.

8. The electromagnetic wave detection device according to claim 7, wherein an image plane by the electromagnetic wave beam diameter changing optical system is located on the optical effect unit.

9. The electromagnetic wave detection device according to claim 1, further comprising a timing adjuster unit which adjusts relative input timing between the probe light pulses and the electromagnetic wave when each of the probe light pulses and the electromagnetic wave is input to the optical effect unit.

10. The electromagnetic wave detection device according to claim 1, further comprising a pump light pulse irradiating unit which converges and irradiates pump light pulses onto an object to be measured and scans said converging and irradiating position in the object to be measured, wherein a terahertz wave is generated in the object to be measured by converging and irradiating pump light pulses onto the object to be measured by the pump light pulse irradiating unit, the terahertz wave and the probe light pulses are input to the optical effect unit, and the photodetector detects the probe light pulses output from the optical effect unit in terms of each converging and irradiating position onto the object to be measured by the pump light pulse irradiating unit.

* * * * *